(12) United States Patent
Cloutier et al.

(10) Patent No.: US 6,521,212 B1
(45) Date of Patent: *Feb. 18, 2003

(54) METHOD FOR TREATING PERIPHERAL VASCULAR DISEASE BY ADMINISTERING BENZINDENE PROSTAGLANDINS BY INHALATION

(75) Inventors: Gilles Cloutier; James Crow; Michael Wade, all of Chapel Hill, NC (US); Richard E. Parker, Spring Hill; James E. Loyd, Nashville, both of TN (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/525,471

(22) Filed: Mar. 15, 2000

Related U.S. Application Data
(60) Provisional application No. 60/124,999, filed on Mar. 18, 1999, and provisional application No. 60/124,999, filed on Mar. 18, 1999.

(51) Int. Cl.[7] .............................. A61K 9/12; A61K 31/19
(52) U.S. Cl. ............................ 424/45; 424/46; 424/489; 514/573; 514/571
(58) Field of Search .......................... 424/45, 46, 489; 514/573, 571

(56) References Cited

U.S. PATENT DOCUMENTS 4,306,075 A  12/1981  Aristoff
5,153,222 A  10/1992  Tadepalli et al.
6,054,486 A  * 4/2000  Crow et al.

FOREIGN PATENT DOCUMENTS

EP  0 159 784 A  10/1985

OTHER PUBLICATIONS

W. M. Zapol et al., Pulmonary Circulation During ARDS, "Pulmonary Circulation During Adult Respiratory Distress Syndrome," pp. 241–273 (1985).
W. W. Fox et al., Pediatrics, "Pulmonary Hypertension in the Perinatal Aspiration Syndromes," vol. 59, No. 2, pp. 205–211 (1977).
A. R. Dworetz et al. Pediatrics, "Survival of Infants With Persistent Pulmonary Hypertension Without Extracorporeal Membrane Oxygenation," vol. 84, No. 1, pp. 1–6 (1989).
G. J. Peckham et al., The Journal of Pediatrics, "Physiologic factors affecting pulmonary artery pressure in infants with persistent pulmonary hypertension," vol. 93, No. 6, pp. 1005–1010 (1978).
R. C. Wetzel, Anesthesiology, "Aerosolized Prostacyclin," vol. 82, No. 6 (1995).

* cited by examiner

Primary Examiner—Jose' G. Dees
Assistant Examiner—M. Haghighatrai
(74) Attorney, Agent, or Firm—Foley & Lardner

(57) ABSTRACT

A method of delivering benzindene prostaglandins to a patient by inhalation is discussed. A benzindene prostaglandin known as UT-15 has unexpectedly superior results when administered by inhalation compared to parenterally administered UT-15 in sheep with induced pulmonary hypertension.

12 Claims, 18 Drawing Sheets

FIG. 5

● AEROSOL UT 15
○ INTRAVENOUS UT 15

Central venous pressure (cmH₂O) vs. dose:
- BASELINE
- UT 15 250 (ng/kg/min)
- UT 15 500 (ng/kg/min)
- UT15 1000 (ng/kg/min)

FIG. 12

● AEROSOL UT 15
○ INTRAVENOUS UT 15

X-axis: BASELINE, U44069, UT 15 250 (ng/kg/min), UT 15 500 (ng/kg/min), UT 15 1000 (ng/kg/min)

Y-axis: SYSTEMIC ARTERIAL PRESSURE (mmHg), 80, 100, 120, 140

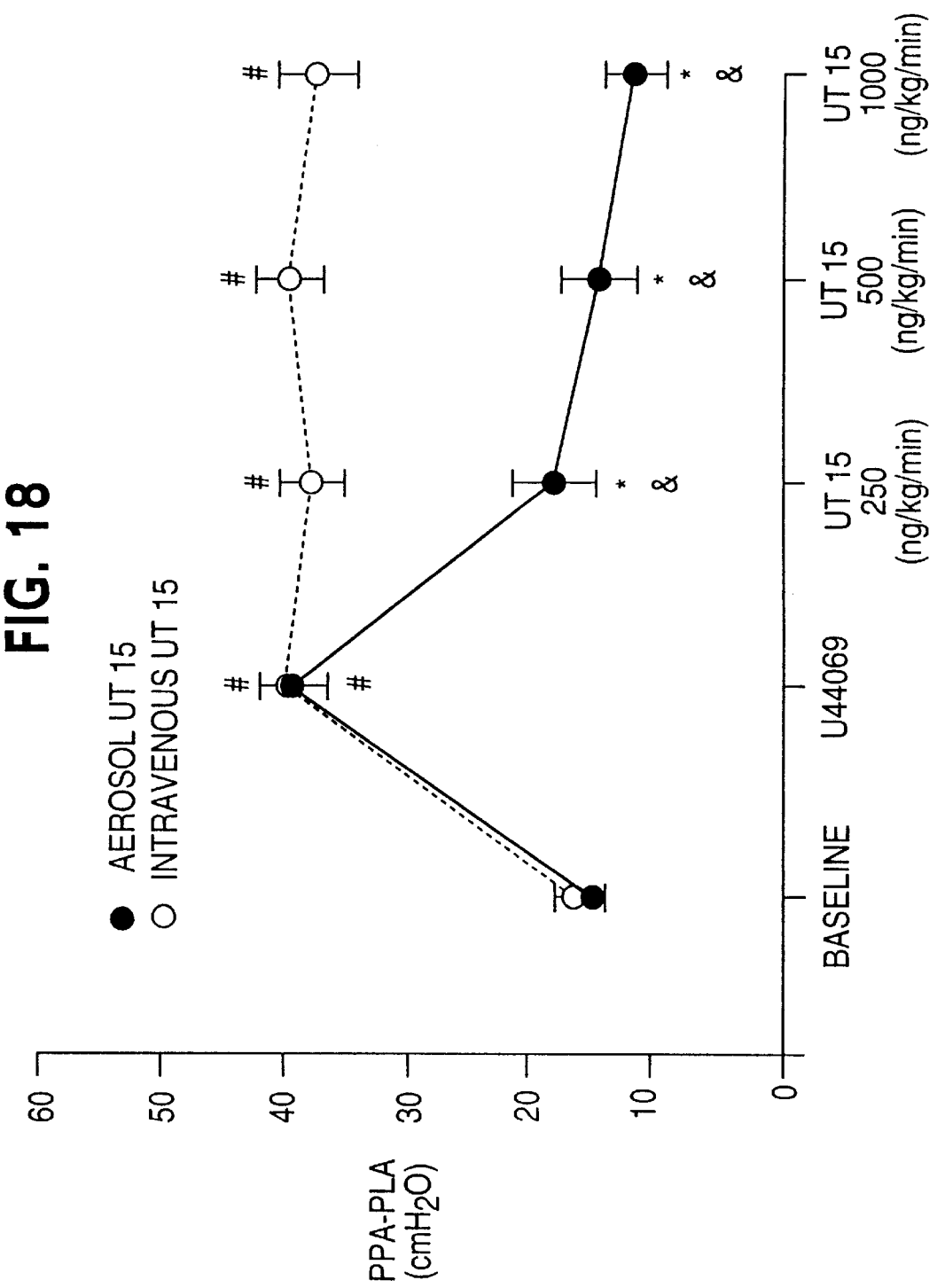

METHOD FOR TREATING PERIPHERAL VASCULAR DISEASE BY ADMINISTERING BENZINDENE PROSTAGLANDINS BY INHALATION

This application claims the benefit of provisional application Serial No. 60/124,999, filed Mar. 18, 1999.

BACKGROUND OF THE INVENTION

Benzindene prostaglandins are now known to be useful to treat a variety of conditions. U.S. Pat. No. 5,153,222 describes the use of a preferred class of benzindene prostaglandins in the treatment of pulmonary hypertension, including both primary and secondary pulmonary hypertension. In particular, this patent discusses the use of the compound 9-deoxy-2',9-alpha-methano-3-oxa-4,5,6-trinor-3,7-(1',3'-interphenylene)-13,14-dihydro-prostaglandin F1 (also known as UT-15).

However, this patent does not specifically suggest the administration of such benzindene prostaglandins by inhalation or the surprising benefits that result from their delivery by inhalation.

U.S. Pat. No. 4,306,075 describes a large group of carbacyclin analogs, including, benzindene prostaglandins which produce various pharmacological responses, such as inhibition of platelet aggregation, reduction of gastric secretion, and bronchodilation. It is indicated that the compounds have useful application as anti-thrombotic agents, anti-ulcer agents, and anti-asthma agents. The patent does mention administration by inhalation. The patent specifically discloses the compound UT-15 in Example 33. However, this patent provides only limited biological data relating to the use of such compounds. At column 59, example 31, the patent discloses a compound that is structurally similar to that of example 33 (UT-15), but it is not the same compound. Example 31 discloses (column 59, lines 41–45) that "[t]he compounds [sic] 9-deoxy-2', 9-methano-3-oxa4,5,6-trinor-3,7-(1',3'-interphenylene)- PGF1, methyl ester, given to a rat orally at a dose of 1 mg/kg lowered blood pressure 44 mmHg. After 52 min the blood pressure was still lower 14 mm."

All blood is driven through the lungs via the pulmonary circulation in order, among other things, to replenish the oxygen which it dispenses in its passage around the rest of the body via the systemic circulation. The flow through both circulations is in normal circumstances equal, but the resistance offered to it in the pulmonary circulation is generally much less than that of the systemic circulation. When the resistance to pulmonary blood flow increases, the pressure in the circulation is greater for any particular flow. This is referred to as pulmonary hypertension. Generally, pulmonary hypertension is defined through observations of pressures above the normal range pertaining in the majority of people residing at the same altitude and engaged in similar activities.

Most often pulmonary hypertension is a manifestation of an obvious or explicable increase in resistance, such as obstruction to blood flow by pulmonary emboli, malfunction of the heart's valves or muscle in handling blood after its passage through the lungs, diminution in pulmonary vessel caliber as a reflex response to hypoventilation and low oxygenation, or a mismatch of vascular capacity and essential blood flow, such as shunting of blood in congenital abnormalities or surgical removal of lung tissue. Such pulmonary hypertension is referred to as secondary hypertension.

There remain some cases of pulmonary hypertension where the cause of the increased resistance is as yet inexplicable. They are described as primary pulmonary hypertension (PPH) and are diagnosed by and after exclusion of the causes of secondary pulmonary hypertension. Despite the possibility of a varied etiology, cases of primary pulmonary hypertension tend to comprise a recognizable entity. Approximately 65% are female and young adults are most commonly afflicted, though it has occurred in children and patients over 50. Life expectancy from the time of diagnosis is short, about 3 to 5 years, though occasional reports of spontaneous remission and longer survival are to be expected given the nature of the diagnostic process. Generally, however, progress is inexorable via syncope and right heart failure and death is quite often sudden.

Pulmonary hypertension refers to a condition associated with an elevation of pulmonary arterial pressure (PAP) over normal levels. In humans, a typical mean PAP is approximately 12–15 mm Hg. Pulmonary hypertension, on the other hand, is sometimes marked by PAP increases by at least 5 to 10 mm Hg over normal levels. PAP readings as high as 50 to 100 mm Hg over normal levels have been reported. When the PAP markedly increases, plasma can escape from the capillaries into the lung interstitium and alveoli. Fluid buildup in the lung (pulmonary edema) can result, with an associated decrease in lung function that can in some cases be fatal.

Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism. Chronic pulmonary hypertension is characterized by major structural changes in the pulmonary vasculature, which result in a decreased cross-sectional area of the pulmonary blood vessels. This may be caused by, for example, chronic hypoxia, thromboembolism, or unknown causes (idiopathic or primary pulmonary hypertension).

Pulmonary hypertension has been implicated in several life-threatening clinical conditions, such as adult respiratory distress syndrome ("ARDS") and persistent pulmonary hypertension of the newborn ("PPHN"). Zapol et al., Acute Respiratory Failure, p. 241–273, Marcel Dekker, New York (1985); Peckham, J. Ped. 93:1005 (1978). PPHN, a disorder that primarily affects full-term infants, is characterized by elevated pulmonary vascular resistance, pulmonary arterial hypertension, and right-to-left shunting of blood through the patent ductus arteriosus and foramen ovale of the newborn's heart. Mortality rates range from 12–50%. Fox, Pediatrics 59:205 (1977); Dworetz, Pediatrics 84:1 (1989). Pulmonary hypertension may also result in a potentially fatal heart condition known as "cor pulmonale", or pulmonary heart disease. Fishman, "Pulmonary Diseases and Disorders" $2^{nd}$ Ed., McGraw-Hill, New York (1988).

The treatment of pulmonary hypertension by the parenteral administration of certain prostaglandin endoperoxides, such as prostacyclin (also known as flolan), is also known and is the subject of U.S. Pat. No. 4,883,812. Prostacyclin has been administered by inhalation and is used to treat pulmonary hypertension by inhalation. Anesthesiology, vol. 82, no. 6, pp. 1315–1317.

SUMMARY OF THE INVENTION

This invention relates to the administration of a therapeutically effective amount of a benzindene prostaglandin to a mammal in need thereof by inhalation. More particularly, the invention relates to a method of treating pulmonary hypertension by administering an effective amount of a benzindene prostaglandin to a mammal in need thereof by inhalation.

Inhalation of benzindene prostaglandins provides unexpectedly superior results compared to parenteral administration of benzindene prostaglandins.

BRIEF DESCRIPTION OF THE DRAWINGS

FIG. 2 depicts the effects of the aerosolized UT15 administered to the sheep intravenously induced with U44069 on systemic arterial pressure (PSA or PSYS); on pulmonary arterial pressure (PPA); and pulmonary vascular resistance (PVR), respectively.

FIG. 5 is the dose-response effect of intravenously infused UT15 and aerosolized UT15 on the central venous pressure during baseline conditions.

FIG. 12 is the dose-response effect of intravenously infused and aerosolized UT15 on systemic arterial pressure during intravenously infused U44069.

FIG. 14 is the dose-response effect of intravenously infused and aerosolized UT15 on left atrial pressure during intravenously infused U44069.

FIG. 17 is the dose-response effect of intravenously infused and aerosolized UT15 on pulmonary vascular driving pressure (PPA minus PLA) during baseline-conditions.

FIG. 18 is the dose-response effect of intravenously infused and aerosolized UT15 on pulmonary vascular driving pressure (PPA-PLA) during intravenously infused U44069.

DETAILED DESCRIPTION OF THE INVENTION

Figure 1:
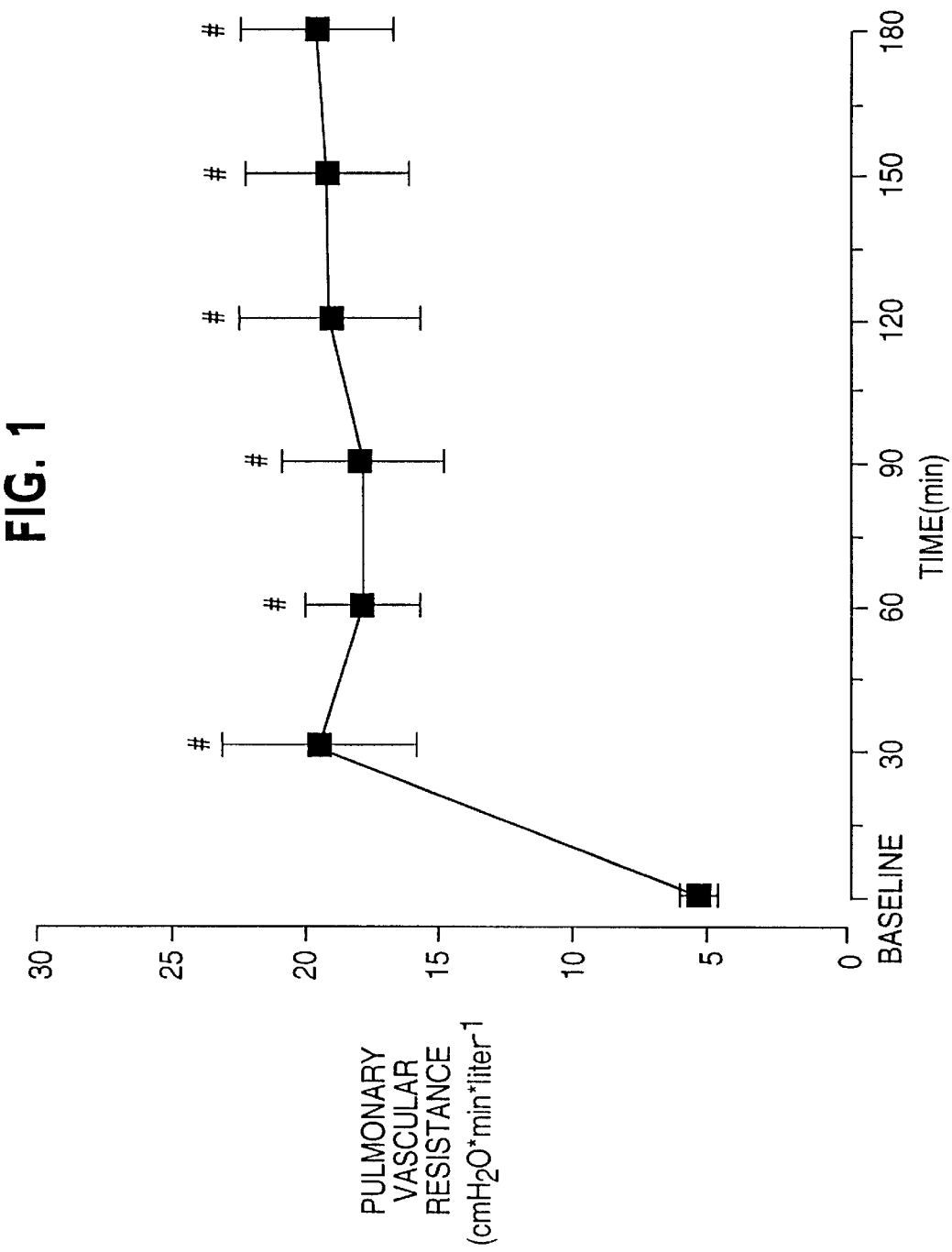
FIG. 1 is a graph of pulmonary vascular resistance ($cmH_2O*min/liter$) intravenously induced by U44069 over time (min).

Unless otherwise specified, all references to "a" or "an" mean at least one.

One embodiment of the present invention is a method of delivering a benzindene prostaglandin or a pharmaceutically acceptable salt or ester thereof to a mammal in need thereof by inhalation.

A preferred group of benzindene prostaglandins for delivery by inhalation according to the present invention is as follows:

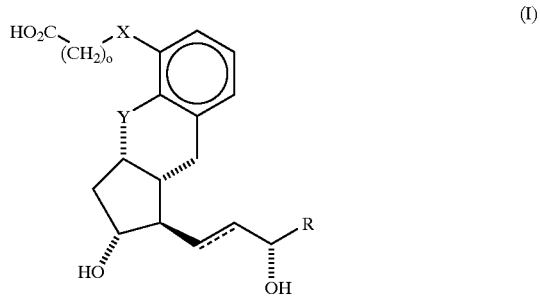

(I)

wherein a is an integer of from 1 to 3; X and Y, which may be the same or different, are selected from —O— and —$CH_2$—; R is —$(CH_2)_5$—$R^1$ wherein $R^1$ is hydrogen or methyl, or R is cyclohexyl, or R is —$CH(CH_3)$ $CH_2C{\equiv}CCH_3$; and the dotted line represents an optional double bond; or a physiologically acceptable salt or acid derivative thereof.

The most preferred benzindene prostaglandin is UT-15, which is 9-deoxy-2', 9-alpha-methano-3-oxa-4,5,6-trinor-3, 7-(1',3'-interphenylene)-13,14-dihydro-prostaglandin F1.

"Inhalation" delivery in the context of this invention refers to the delivery of the active ingredient or combination of active ingredients through a respiratory passage, wherein the mammal in need of the active ingredient(s) inhales the active ingredient(s) through the mammal's airways, such as the nose or mouth.

Active ingredients, which are aerosolized, atomized, and/or nebulized for delivery by inhalation according to the present invention include liquid formulations comprising a benzindene prostaglandin, such as UT-15, alone or in combination with other active ingredients described below. UT-15 may be used as a free acid or in the form of a pharmaceutically acceptable salt or ester or other acid derivative. In addition, sustained release formulations comprising UT-15 may be used, including PEGylated forms and/or protein-conjugated forms of UT-15.

The term "acid derivative" is used herein to describe $C_1$–$C_4$ alkyl esters and amides, including amides wherein the nitrogen is optionally substituted by one or two $C_1$–$C_4$ alkyl groups.

The invention also includes bioprecursors or "pro-drugs" of UT-15, that is, compounds which are converted in vivo to UT-15 or its pharmaceutically active derivatives thereof.

Further aspects of the present invention are concerned with the use of UT-15, or a pharmaceutically acceptable salt or acid derivative thereof, in the manufacture of a medicament for the treatment of peripheral vascular disease The present invention extends to non-physiologically acceptable salts of UT-15 which may be used in the preparation of the pharmacologically active compounds of the invention. The physiologically acceptable salts of UT-15 include salts derived from bases.

Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

Optionally, one or more pharmaceutically acceptable carriers or excipients may be included in the formulation to be aerosolized, atomized, or nebulized according to the invention.

A preferred solution for administration by inhalation with a nebulizer includes a sterile solution of UT-15 comprising UT-15, sodium citrate, citric acid, sodium hydroxide, sodium chloride, and meta-cresol. A more preferred solution is prepared by mixing 0.125 grams UT-15, 1.25 grams hydrous sodium citrate, 0.125 grams of anhydrous citric acid, 0.05 grams of sodium hydroxide, and approximately 250 ml of water for injection.

Preferably, a nebulizer, inhaler, atomizer or aerosolizer is used which forms droplets from a solution or liquid containing the active ingredient(s). The droplets are preferably less than 10 micrometers in diameter. One preferred nebulizer is the AM-601 MEDICATOR AEROSOL DELIVERY SYSTEM™ (a nebulizer manufactured by Healthline Medical in Baldwin Park, Calif.).

Alternatively, solid formulations, usually in the form of a powder, may be inhaled in accordance with the present invention. In such case, the particles are preferably less than 10 micrometers in diameter, and more preferably, less than 5 micrometers in diameter.

This invention further relates to delivering a benzindene prostaglandin and/or its salts or esters by inhalation for applications where inhalation delivery is appropriate for the treatment of that particular condition. Benzindene prostaglandins, including UT-15 and its salts or esters, have been shown to be useful for multiple applications. For example, UT-15 has been shown to exhibit a potent anti-aggregatory action on blood platelets, and therefore has a particular utility in mammals as an anti-thrombotic agent. Further known uses of UT-15 include treatment of peripheral vascular disease (covered in co-pending application Serial No. 09/190,450, now U.S. Pat. No. 6,054,486, the entire contents of which are incorporated by reference herein). In the case of treating peripheral vascular disease by inhalation of a benzindene prostaglandin of the present invention, the dosage for inhalation, taking into account that some of the active ingredient is breathed out and not taken into the bloodstream, should be sufficient to deliver an amount that is equivalent to a daily infusion dose in the range of 25 $\mu$g to 250 mg; typically from 0.5 tg to 2.5 mg, preferably from 7 $\mu$g to 285 $\mu$g, per day per kilogram bodyweight. For example, an intravenous dose in the range 0.5 $\mu$g to 1.5 mg per kilogram bodyweight per day may conveniently be administered as an infusion of from 0.5 ng to 1.0 $\mu$g per kilogram bodyweight per minute. A preferred dosage is 10 ng/kg/min.

Benzindene prostaglandins, including UT-15 and its salts or esters, may also be administered according to the present invention by inhalation to reduce and control excessive gastric secretion, thereby reducing or avoiding gastrointestinal ulcer formation, and accelerating the healing of ulcers and lesions already present in the gastrointestinal tract. In addition, benzidene prostaglandins may also be administered according to the present invention by inhalation to treat congestive heart failure, to reduce inflammation and/or pulmonary hypertension associated with lung transplants[,].

Benzindene prostaglandins, including UT-15 and its salts or esters, further exhibit vasodilatory action on blood vessels and therefore have a particular utility as anti-hypertensives for the treatment of high blood pressure in mammals, including man. Use as an anti-hypertensive (or hypotensive agent) may be accomplished by administering a pharmaceutical composition containing a benzindene prostaglandin, including UT-15.

Benzindene prostaglandins, including UT-15, may be used according to the present invention by inhalation to treat any condition where it is desired to reduce blood pressure, inhibit platelet aggregation, to reduce the adhesive character of platelets, and/or to treat or prevent the formation of thrombi in mammals, including man. For example, they may be used in the treatment and prevention of myocardial infarcts and in the treatment of peripheral vascular disease, to treat and prevent post-operative thrombosis, to promote patency of vascular grafts following surgery, and to treat complications of arteriosclerosis and conditions such as atherosclerosis, blood clotting defects due to lipemia, and other clinical conditions in which the underlying etiology is associated with lipid imbalance or hyperlipidemia. Moreover, benzidene prostaglandins, including UT-15 and its salts or esters, have a further utility in the promotion of wound healing in mammals, including man.

Benzindene prostaglandins, including UT-15 and its salts or esters, may also be used as additives to blood, blood products, blood substitutes, and other fluids, which are used in artificial extra-corporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of UT-15. For this purpose, UT-15 or its salts or esters may be introduced by inhalation until it reaches a level in the circulating blood, the blood of the donor animal, or the blood of the perfused body portion, or to two or all of those equivalent to a steady state dose of 0.001 micrograms to 10 micrograms, per liter of circulating fluid. Another embodiment is to use UT-15 in laboratory animals, e.g., cats, dogs, rabbits, monkeys and rats, for these purposes in order to develop new methods and techniques for organ and limb transplants.

In accordance with the present invention, a benzindene prostaglandin is delivered by inhalation to a patient in need thereof in a "therapeutically effective amount". A "therapeutically effective amount" refers to that amount that has therapeutic effects on the condition intended to be treated or prevented. For example, an "antihypertensive effective amount" refers to that amount in which the effects from pulmonary hypertension, and particularly, pulmonary arterial pressure (PAP), are reduced towards a normal level relative to hypertensive levels, or maintained at normal levels. The precise amount that is considered effective for a particular therapeutic purpose will, of course, depend upon the specific circumstances of the patient being treated and the magnitude of effect desired by the patient's doctor. Titration to effect may be used to determine proper dosage.

Such formulations, both for veterinary and for human medical use, of the present invention comprise the active ingredient, a benzindene prostaglandin or salt or ester thereof, together with one or more pharmacologically acceptable carriers therefore and optionally other therapeutic ingredients. The carrier(s) must be "acceptable" in the sense of being compatible with the other ingredients of the formulation and not deleterious to the recipient thereof.

Furthermore, the formulations may conveniently be presented in unit dosage form and may be prepared by any of the methods well known in the art of pharmacy. All methods include the step of bringing into association the active ingredient with the carrier which constitutes one or more pharmacologically acceptable accessory ingredients.

The invention further relates to a method of treating pulmonary hypertension by inhalation of a benzindene prostaglandin. "Pulmonary hypertension" refers to both acute and chronic hypertension, including primary pulmonary hypertension and secondary pulmonary hypertension, and is associated with an elevated pulmonary arterial pressure over normal levels.

The efficacy of benzindene prostaglandins, such as UT-15, for treating pulmonary hypertension can be assessed by determining the hemodynamics associated with pulmonary hypertension. In particular, measurements of pulmonary arterial pressure (PPA), left atrial pressure (PLA), central venous pressure (PCV), systemic arterial pressure (PSYS), heart rate (HR), and cardiac output (CO) are useful in determining the effects of benzindene prostaglandins delivered by inhalation or parenterally.

Although pulmonary arterial pressure can be directly measured and is often used to quantify pulmonary arterial hypertension, PPA can be affected by 3 other variables: Co, PLA and PVR, as indicated by Equation 1:

$$PPA=(CO*PVR)+PLA \quad (1)$$

As can be seen from Equation 1, PPA can be elevated by increases in PLA (e.g., left heart failure, mitral valve stenosis, mitral valve regurgitation), increases in CO (e.g., low hematocrit, peripheral vasodilation, left to right shunt, etc.), and by increases in PVR (decreased pulmonary vascular surface area, decreased pulmonary vascular radii, pulmonary vascular obstructions, etc.).

On the other hand, PVR can not be directly measured and must be calculated by the following Equation 2:

$$PVR=(PPA-PLA)/CO \quad (2)$$

PVR is a better index of pulmonary arterial hypertension (PAH), since interventions used to treat PAH are best if they only affect PVR and have no or little effect on CO and PLA.

Heart rate was determined by measuring the time (seconds) required for 25 heart beats to occur ($t_{25}$) as indicated by the pulsations on the blood flow meter; the beats per minute (BPM) were calculated by the following equation:

$$BPM=(25\ beats/t_{25})*60\ seconds$$

All pressure may be monitored by commercially available transducers, such as Model 1290A HEWLETT PACKARD™ transducer (Andover, Me.), which is attached to VALIDYNE CD19A Carrier Dmod. Amplifiers (Northridge, Calif.). Cardiac output may be measured by a Transonic Systems T101 Ultrasonic Bloodflow. Meter (Ithaca, N.Y.).

The pressure and blood flow signals may be recorded on ASTROMED MT-9500 Stripchart Recorder (West Warwick, R.I.) and digitally recorded with a personal-computer using Easy Data Acquisition Software (Nashville, Tenn.).

It has been discovered that aerosolized UT-15 has both greater potency and efficacy relative to attenuating chemically induced pulmonary hypertension as shown by an increase in pulmonary vascular resistance. Furthermore, aerosolized UT-15 has a greater potency as compared to intravascularly administered UT-15, since the actual amount of UT-15 delivered via aerosolization delivery is only a fraction (10–50%) of the dosage delivered intravascularly. While the mechanism(s) that accounts for the greater potency and efficacy for aerosolized UT-15 is unknown, it can be hypothesized that a low "first-pass" uptake via intravenous infusion of UT-15 could be at least partially responsible. A low first-pass uptake would thus allow the majority of the drug to be made available to the peripheral circulation (including the coronary circulation), which would increase the heart rate and cardiac output.

Aerosolized UT-15 has no apparent peripheral effects, such as on the heart rate or cardiac output, as compared to intravascular UT-15 during pulmonary vascular hypertension by chemical inducement. This is particularly beneficial for those patients that are near right heart failure and where peripheral vasodilation would exacerbate the challenge to the right heart. On the other hand, if cardiac output is compromised due to right heart failure, then aerosolized prostaglandin would decrease PVR and could allow cardiac output to increase while allowing lowering the load upon the right heart.

The following examples are provided by way of an illustration of the present invention and should in no way be construed as constituting a limitation thereof.

EXAMPLES

Example I

Animal Model

Inhalation solutions were prepared by combining 1.25 grams of Sodium Citrate (Hydrous), 0.125 Citric Acid (Anhydrous), 0.05 grams of Sodium Hydroxide (NF/BP), 0.125 grams of UT-15, and approximately 250 ml of Water for Injection according to the following steps.

1. Measured approximately 210 ml of water into a sterile siliconized glass beaker with a magnetic stir bar
2. Added sodium citrate. Mixed until dissolved.
3. Added citric acid to Step 2 solution. Mixed until dissolved.
4. Measured 12.5 ml of water into sterile plastic tube. Added sodium hydroxide. Mixed until dissolved.
5. Added UT15 to Step 4 solution. Mixed by hand until dissolved.
6. Added the Step 5 solution to Step 3 solution and mixed.
7. pH was adjusted using hydrochloric acid and/or sodium hydroxide solutions to a value of 7.3
8. Final solution was filtered using sterile microfilter into another sterile beaker, then 5 ml of solution was aliquoted to sterile stoppered blood test tubes.
9. Solutions were double boxed and put in −4 degrees Celsius freezer.
10. Placebo solution made up as described above except UT-15 not added and quantities adjusted to make only 50 ml. Working solution was made by adding sterile saline to dilute the UT15 stock solution or placebo to the desired amount (depending on dose desired, weight of sheep, and duration of aerosolizing). This solution was then added to the nebulizer in volumes not exceeding 5 ml until entire amount was used.

For a 35 kg sheep at a UT-15 dose of 250 ng per kg per minute for 30 minutes, the calculations used were, Calculations: 250×35×30=262,500 ng of UT-15 or 262.5 micrograms of UT-15. The nebulization rate was 0.28 ml per minute, thus 8.4 ml of solution was needed containing 262.5 micrograms of UT-15. However, an amount of solution is needed for the "void" volume (volume always left in the nubulizer). Thus a volume of 9 ml containing a total of 281.25 micrograms of UT-15 (or 0.5625 ml of the stock solution) was made up.

0.5625 ml of UT-15 was measured and added to 8.4375 of sterile saline. This was nebulized over exactly 30 minutes.

Sheep were used as the animal model of choice for these experiments for a number of reasons. First is the docile nature of sheep. They will stand quietly in metabolic cages without having to utilize tranquilizing drugs, which have the potential to complicate experimental results. Second, sheep are large enough to allow direct measurement of CO, PPA, PLA, PCV, and PSYS. Sheep are also large enough to allow direct aerosolization of substances into the lung via tracheostomy thereby preventing swallowing of drugs and thus eliminating a possible secondary route of administration of UT-15. Third, sheep can tolerate a great amount of instrumentation with little or no discomfort. Fourth, sheep have been utilized for several years as an animal model of pulmonary arterial hypertension and thus, there is a great amount of historical data with which to compare the results.

The agent chosen to induce pulmonary arterial hypertension was a PGH2 analog, U44069 (9,11-dideoxy,9α,11α-epoxymethanoprostaglandin $F_{2\alpha}$). The reasons for using U44069 are that it is a very potent pulmonary vasoconstrictor, its characteristics are very similar to endogenously formed thromboxane A2, and it can be titrated to induce the desired degree of pulmonary vasoconstriction. U44069 was mixed with sterile normal saline immediately prior to being used and was protected from light by wrapping the solution with aluminum foil. The concentration of U44069 was adjusted such that a minimal flow rate of 0.8 ml per min was being infused into the sheep. This was done because more concentrated U44069 would have to be infused at very low rates and often causes "pulses" of U44069 due to the infusion characteristics of roller pumps. The U44069 pulses cause vasoconstriction "spikes" and thus would create induce a non-steady-state.

Surgical Procedures

Six yearling sheep (3 males, 3 females; 21–37 kg) were fasted 18–24 hours and initially anesthetized with a short acting barbiturate (thiopental) to allow intubation of the sheep. Halothane gas anesthesia (1.5–2.5%) was then used for the surgical procedures. Via a left thoracotomy, a Transonic blood flow probe was placed around the main pulmonary artery, silastic catheters placed in the main pulmonary artery and left atrium. After approximately 7 days the sheep were reanesthetized and the left carotid artery cannulated, a Cordis Introducer Sheath inserted in the left jugular vein, and a tracheotomy made. The sheep were allowed to recover for another 3–5 days prior to experimentation. These sheep were used to allow measurement of pulmonary arterial pressure (PPA), left atrial pressure (PLA), central venous pressure (PCV), systemic arterial pressure (PSYS), heart rate (HR), and cardiac output (CO) after baseline measurements were made for a minimum of 30 minutes.

Example II

EFFECTS OF PROLONGED U44069 INTRAVENOUS INFUSION ON PULMONARY VASCULAR RESISTANCE

In four sheep, the ability of U44069 to maintain a steady-state increase in PVR was determined. After a 30 minute baseline, U44069 was infused at a rate of 1 microgram per kg of body weight per minute for 180 minutes. As can be seen by FIG. 1, the increase in PVR induced by intravenously induced U44069 is very stable over 3 hours. (In the figures, all data are given as mean ±SEM. "*" indicates significantly different from corresponding intravenously infusion UT-15 delivery rate. "#" indicates significantly different from corresponding baseline value. "&" indicates significantly different from corresponding U44069 value.) Statistical analysis was also tested using multiple paired t-tests, which are not as rigorous as One-way ANOVA/Dunnett's test. In particular, FIG. 1 illustrates that intravenously infused U44069 causes PVR to reach a steady-state increase by 30 minutes and that the steady-state increase lasts for a minimum of 180 minutes. U44069 caused significant alterations in other variables (data not shown) over the 180 minute infusion period relative to their baseline values: PPA increased, HR decreased, CO decreased. PSYS increased above baseline values, however, the differences were not statistically different except at 120, 150 and 180 minutes during U44069 infusion. PCV also increased during U44069 infusion, however, the increases were only significant at 30 and 60 minutes. PLA did not significantly change at any of the time points investigated.

Since all of the U44069 time values were different from baseline yet none were different from each other as determined by the paired t-tests, this would argue strongly that there were no differences at any of the time points during U44069 infusion. These data would indicate that any alterations in PVR by UT-15 is due to the effects of UT-15 and not complicated by waning of the vasoconstrictor response.

Example III

EFFECTS OF AEROSOLIZED UT-15 GIVEN AT HIGH DOSES ON BASELINE HEMODYNAMICS

Baseline measurements consisted of 30 minutes of monitoring during vehicle/saline aerosolization (0.28 ml/min). After baseline measurements, the vehicle/saline solution in the aerosol delivery system was replaced with the stock UT-15 solution (500 ng/ml) and was aerosolized at 0.28 ml/min for 90 minutes.

Figure 2:
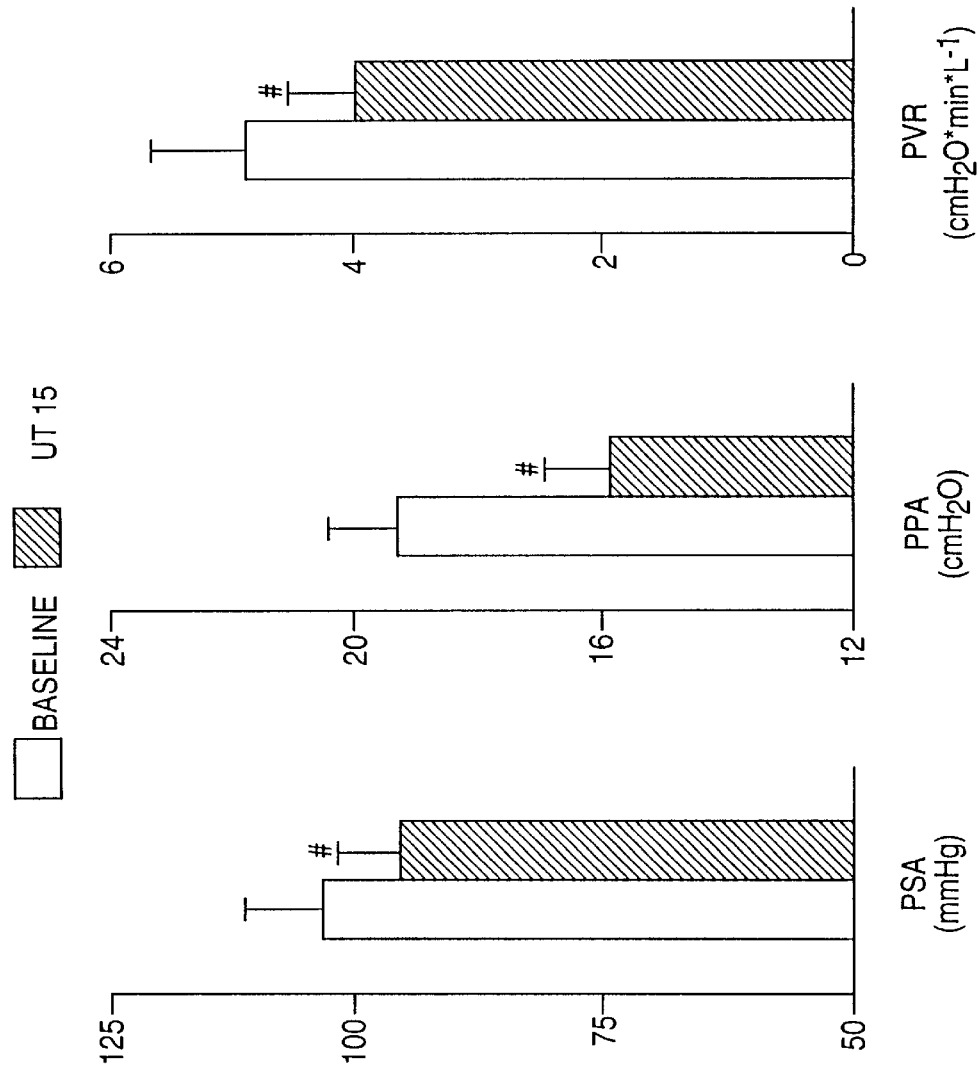
FIG. 2 describes the effects of a high dose of UT15, given as an aerosol, on the hemodynamic variables of the sheep. Specifically.

FIG. 2 depicts the only statistically altered variables observed after 90 minutes of high dose aerosolized UT-15 (3800–5700 ng per kg per min). PSYS decreased by 7.5%, PPA decreased by approximately 18%, and PVR decreased by approximately 19% relative to their respective baseline values.

These data are important in that this would indicate that, unlike intravenously infused UT-15, aerosolized UT-15 can be given in high doses without significant non-lung effects, i.e., heart rate, cardiac output. The aerosol delivery of UT-15 for these experiments is approximately 15–27 times that of the effective minimal tested dose of 250 ng per kg per min shown in FIG. 16.

Example IV

CONTROL INTRAVENOUS UT-15 AND CONTROL AEROSOLIZED UT-15 DOSE RESPONSE EFFECTS ON BASELINE HEMODYNAMICS

Two separate experiments were conducted to determine the dose response effects of intravenously infused UT-15 on baseline hemodynamics and aerosolized UT-15 on baseline hemodynamics. For the infusion experimental protocol, after a 30 minute baseline was established, UT-15 was infused intravenously at 3 rates (250, 500 and 1000 ng per kg per min). In three sheep, the infusion rates lasted for 30 minutes each, and for the other three sheep, the infusions were for 60 minutes each.

The aerosolized UT-15 protocol involved establishing a 30 minute baseline, then administering aerosolized UT-15 via a tracheostromy at rates of 250, 500 and 1000 microgram per kg of body weight per min and at an aerosolization rate of 0.28 ml/min. Again, three sheep were aerosolized for 30 minutes and the other three sheep were aerosolized for 60 minutes.

Figure 3:
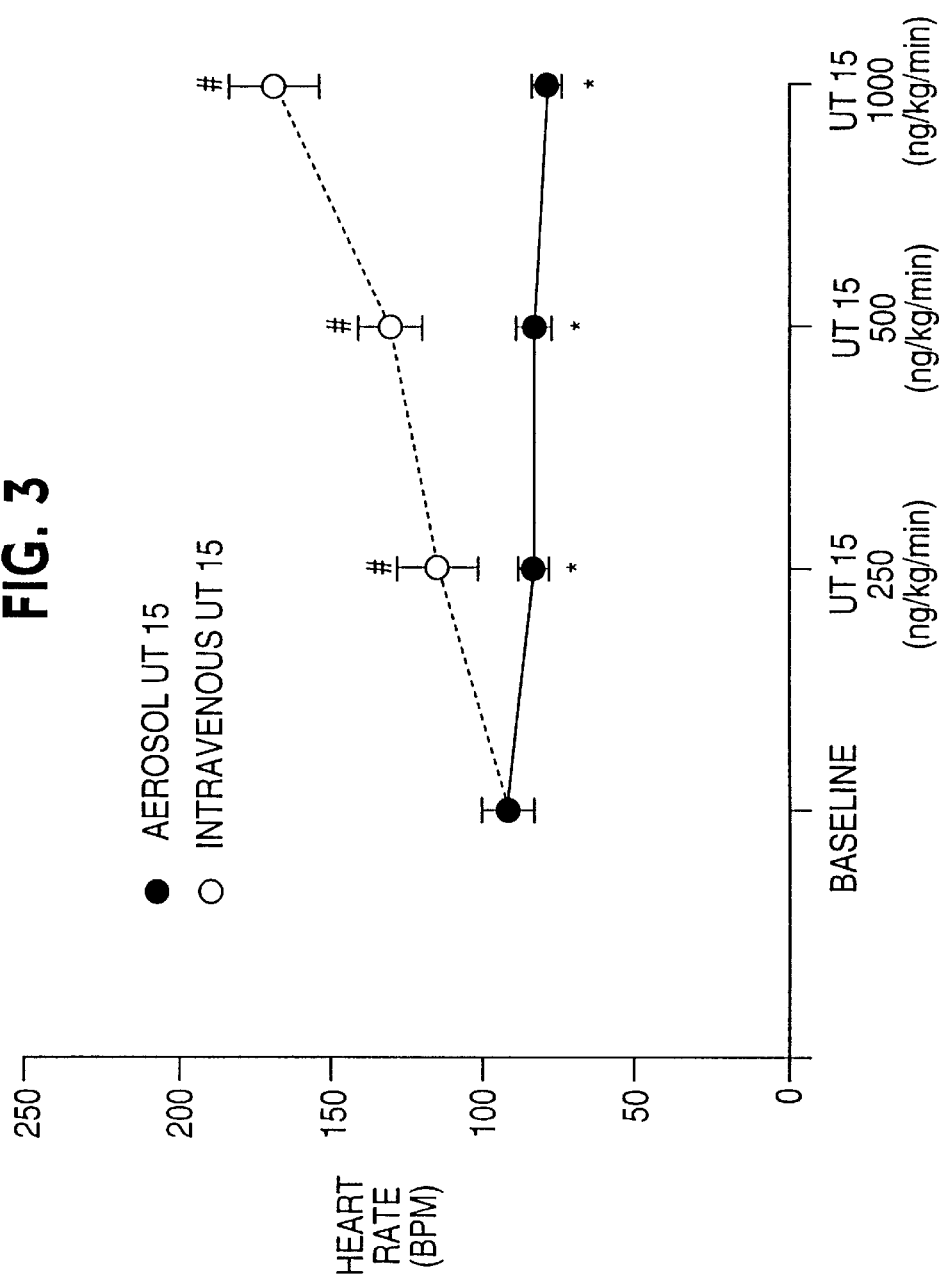
FIG. 3 is the dose-response effect of intravenously infused UT15 and aerosolized UT15 on the heart rate during baseline conditions.

No differences were found between 30 minute and 60 minute UT-15 delivery at each of the 3 rates of administration. FIG. 3 shows the dose-response of intravenously infused and aerosolized UT-15 on heart rate. Heart rate significantly increased during intravenous administration of UT-15 at 250, 500 and 1000 ng per kg per min. Aerosolized UT15 had no effect on heart rate. There was a significant difference between aerosolized and intravenously infused UT-15 at each of the 3 rates of administration.

Figure 4:
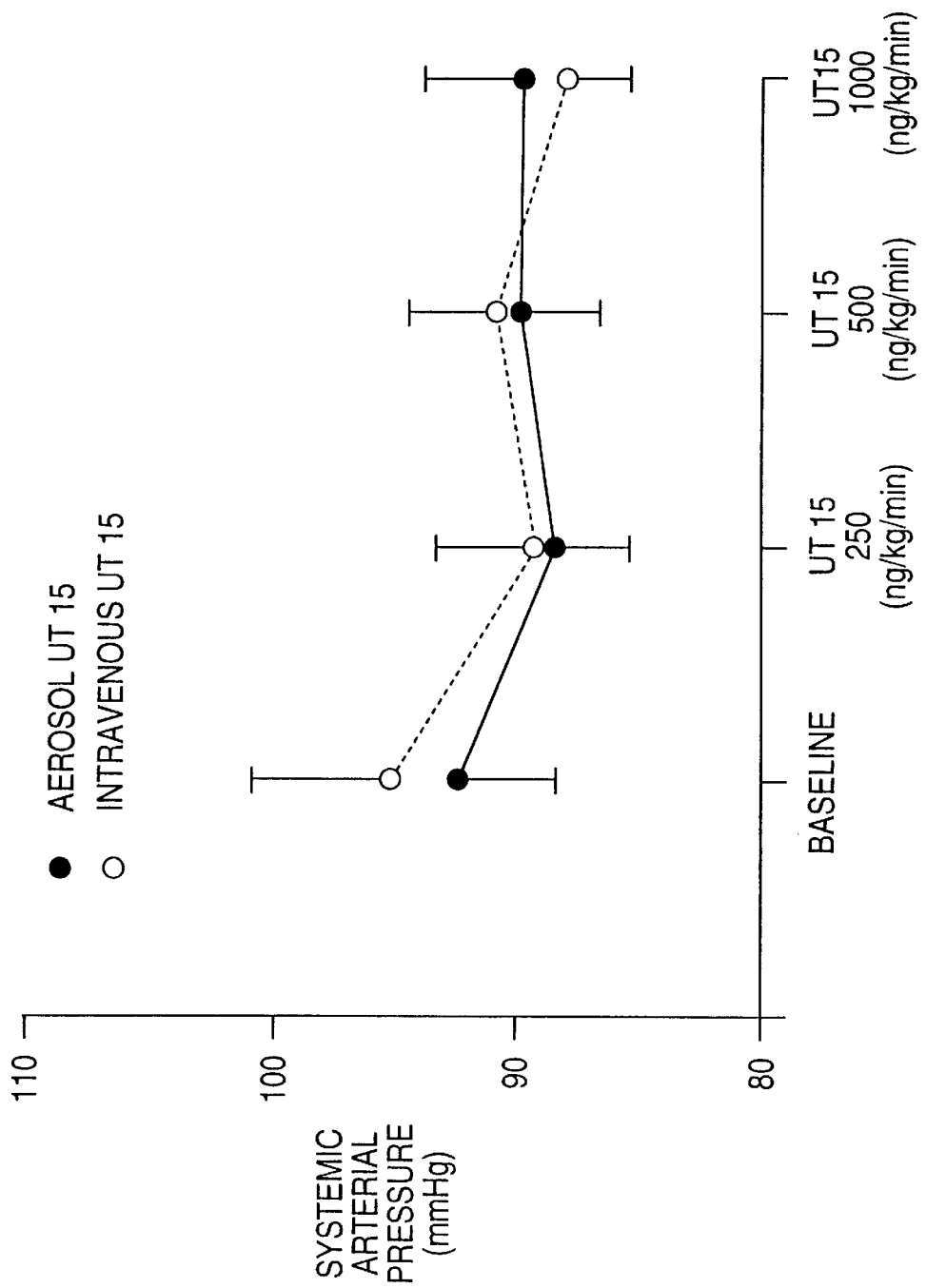
FIG. 4 is the dose-response effect of intravenously infused UT15 and aerosolized UT15 on the systemic arterial pressure during baseline conditions.

FIG. 4 shows that both aerosolized and intravenous UT-15 had no significant effect on PSYS at any of the administration rates used.

Figure 6:
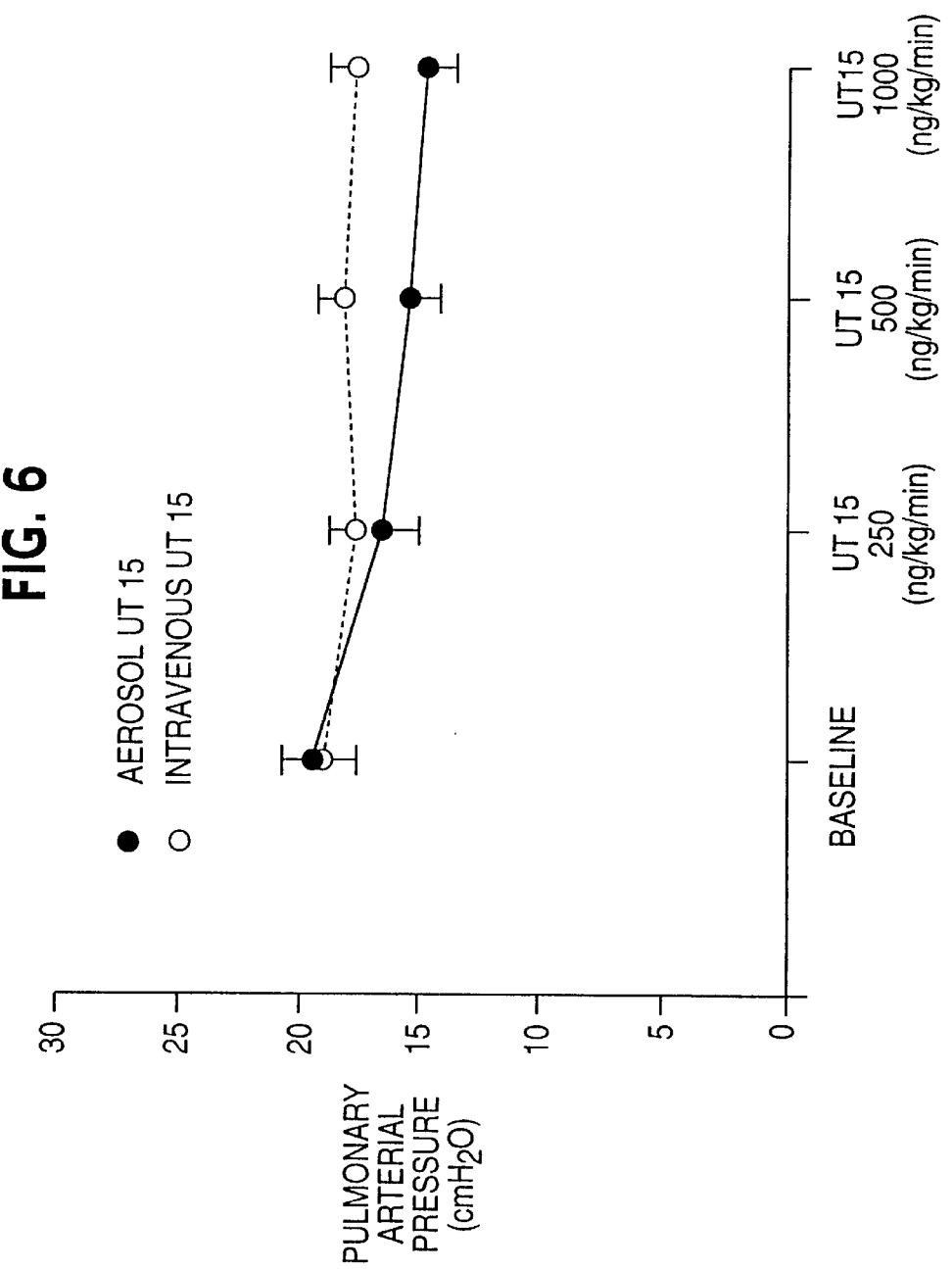
FIG. 6 is the dose-response effect of intravenously infused UT15 and aerosolized UT15 on the pulmonary arterial pressure during baseline conditions.

The effects of UT-15 on PCV are depicted by FIG. 5. There were no statistical difference at any dose relative to its baseline value nor between intravenous and aerosol administered UT-15 at any respective dose. The same effects were also observed for PPA as indicated by FIG. 6, although there was a general trend for PPA to decrease when UT-15 was aerosolized.

Figure 7:
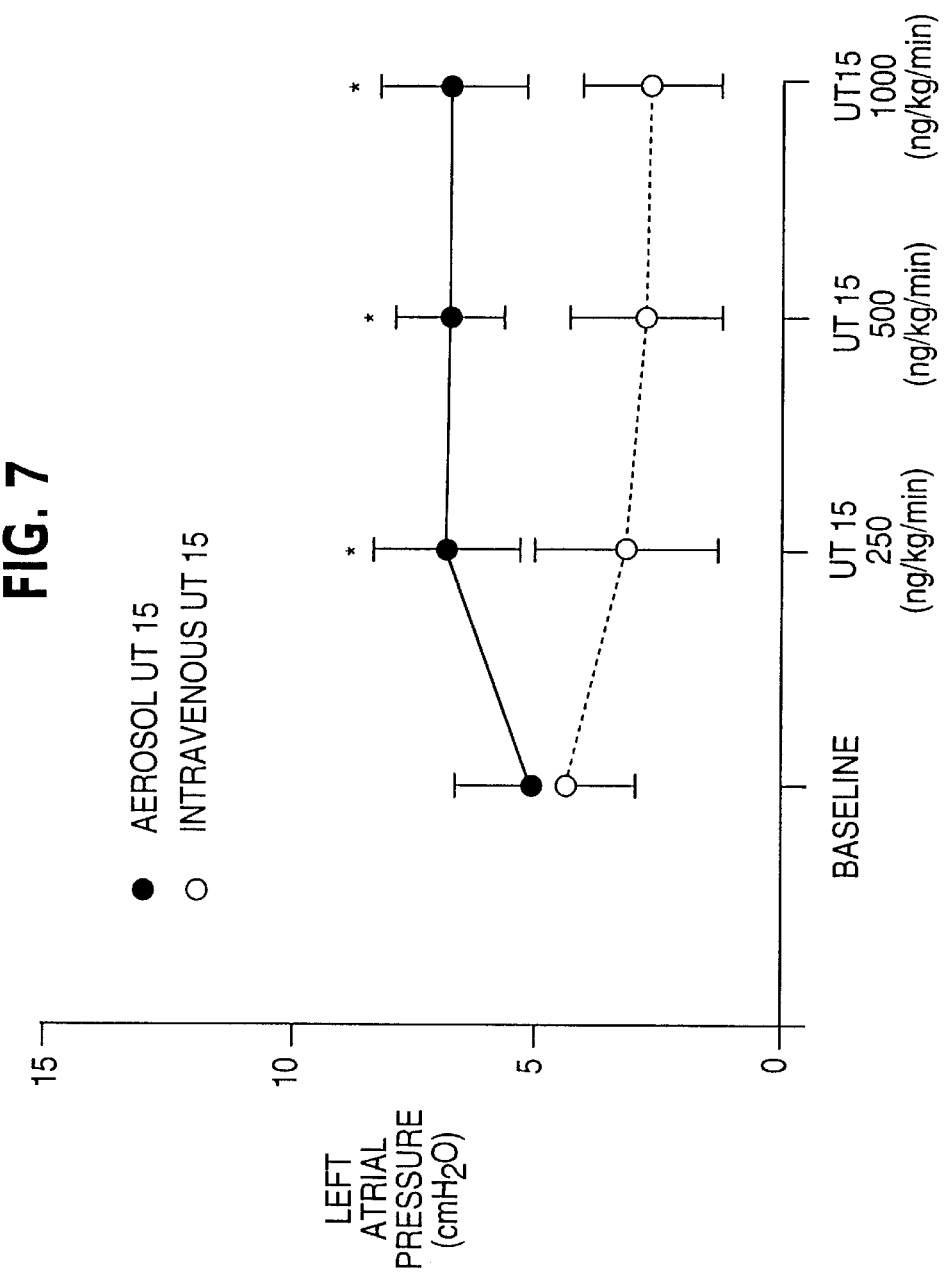
FIG. 7 is the dose-response effect of intravenously infused UT15 and aerosolized UT15 on the left atrial pressure during baseline conditions.

Interestingly, while neither intravenous nor aerosolized UT-15 caused PLA to significantly change from their respective baselines (although the mean values increased during aerosol delivery and decreased for intravenous delivery), there were significant differences between aerosolized and intravenous administered UT-15 at each of the delivery rates. See FIG. 7.

Figure 8:
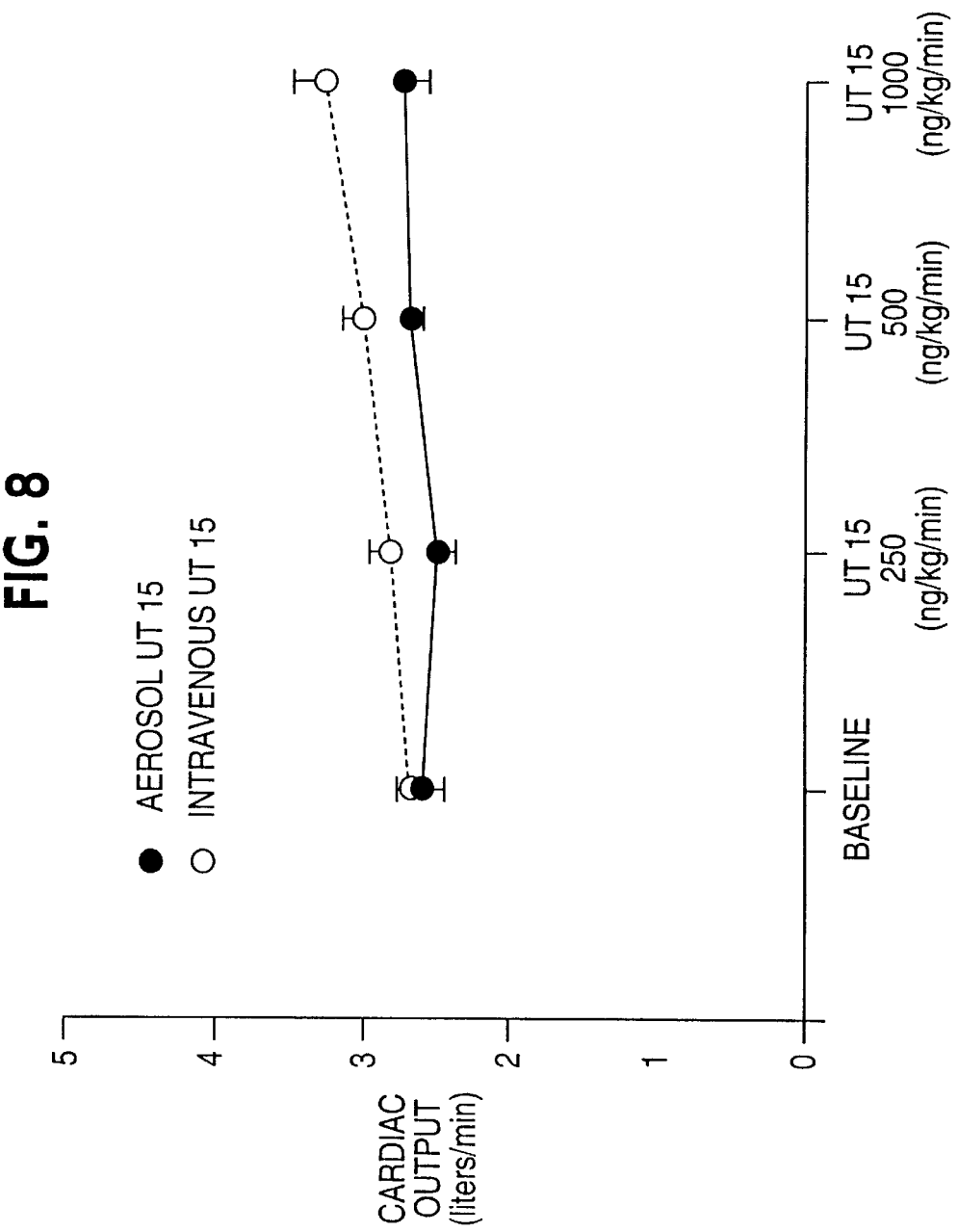
FIG. 8 is the dose-response effect of intravenously infused UT15 and aerosolized UT15 on cardiac output during baseline conditions.

FIG. 8 depicts the effects on CO: no significant changes were observed for any delivery rate relative to the respective baseline values nor were any significant changes observed between the two modes of drug delivery.

Figure 9:
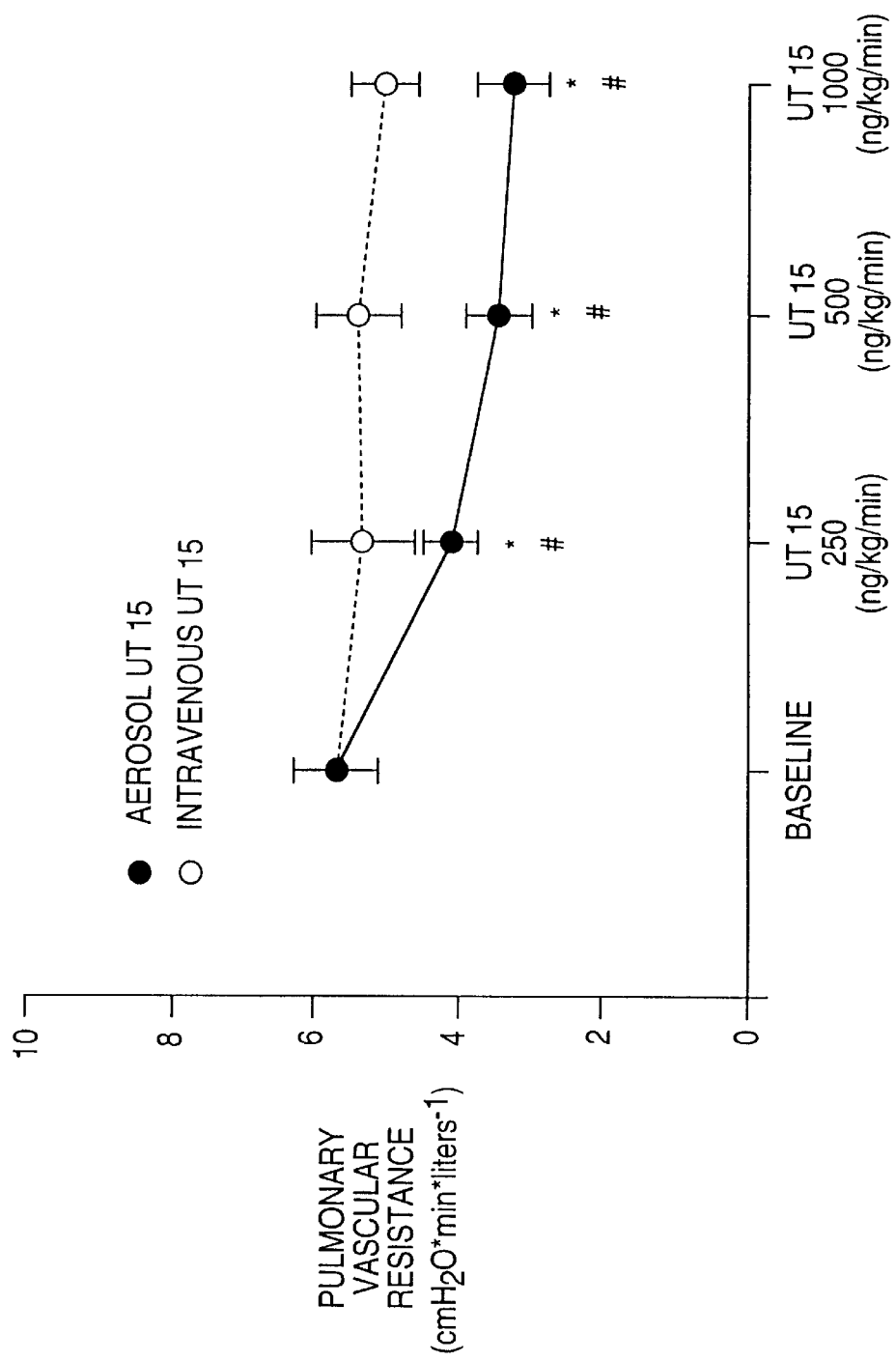
FIG. 9 is the dose-response effect of intravenously infused UT15 and aerosolized UT15 on pulmonary vascular resistance during baseline conditions.

FIG. 9 represents the overall effect of aerosolized and intravenously infused UT-15 on the pulmonary circulation, PVR. Intravenous UT-15 had no significant effect on PVR whereas aerosolized UT-15 did cause a significant decrease at all 3 delivery rates.

Figure 17:
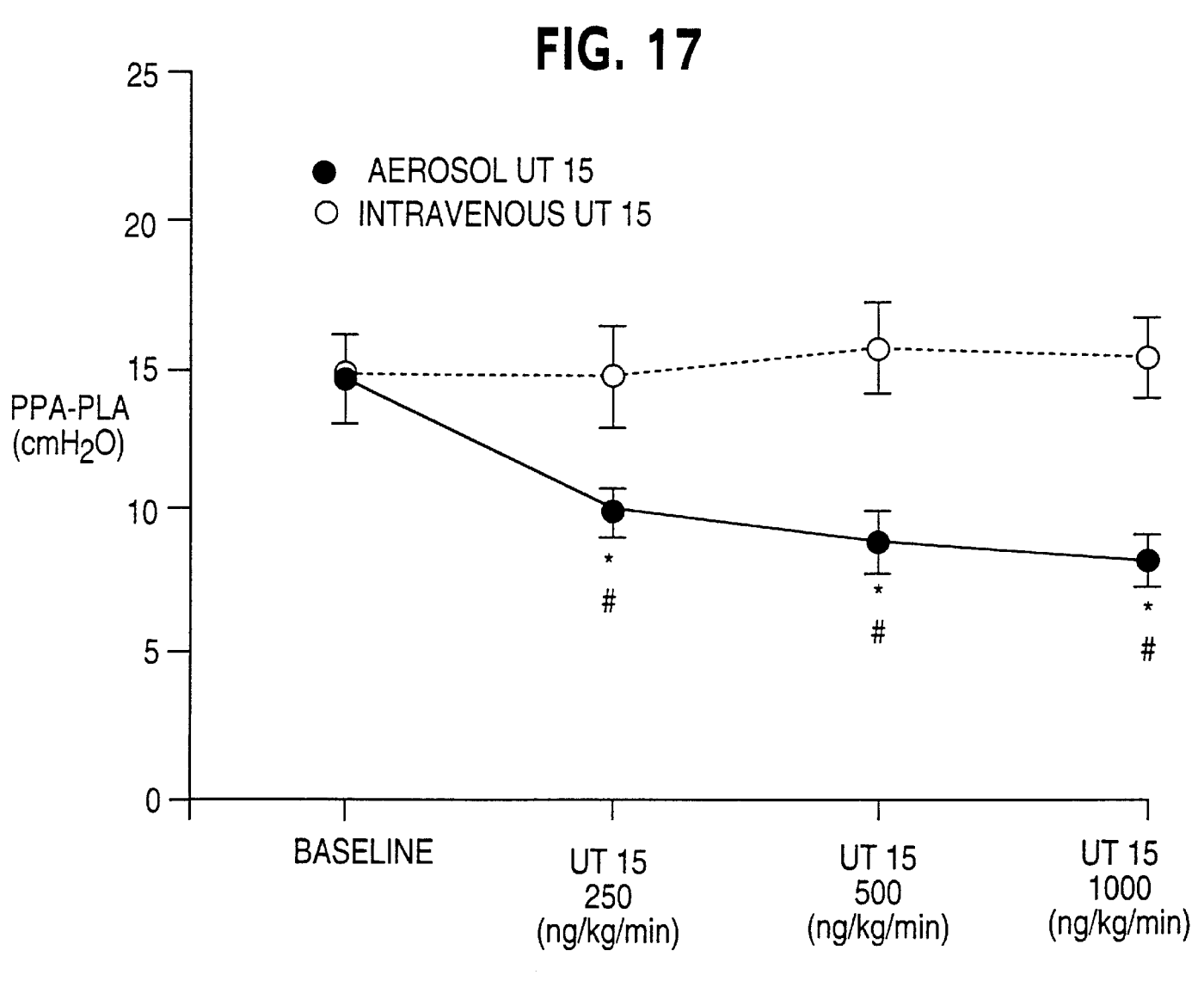

The decrease in PVR for aerosolized UT-15 at 250, 500, and 100 ng per kg per min is attributable to the small increase in PLA and small decrease in PPA. While neither of these variables were significantly different from the baseline values, the combinations (i.e., PPA minus PLA, used in Equation 2) were significant, as depicted in FIG. 17. Intravascularly infused UT-15 had no effect on PVR yet did have significant effects on heart rates. The statistical analysis of these data were done using rigorous two-way ANOVA and Student-Newman-Keuls tests, thus any statistical differences can be accepted with confidence.

Example V

CONSTRICTED INTRAVENOUS AND AEROSOLIZED UT-15 DOSE RESPONSE

Two separate experiments were conducted to determine the dose response effects of intravenously infused UT-15 and aerosolized UT-15 during U44069 induced pulmonary hypertension. After a 30 minute baseline was established, U44069 was infused intravenously at a rate of 1 ng per kg per min. For the intravenous administration of UT-15 and after allowing the sheep to achieve a steady-state for 30–60 minutes, a dose-response to intravenous UT-15 was similar to that set forth in Example IV. For the aerosolized administration of UT-15 and after allowing the sheep to achieve a steady-state for 30–60 minutes, a dose-response to intravenous UT-15 was similar to that set forth in Example IV. In each experimental protocol, UT-15 was administered to three sheep for 30 minutes and to the other three sheep for 60 minutes.

Figure 10:
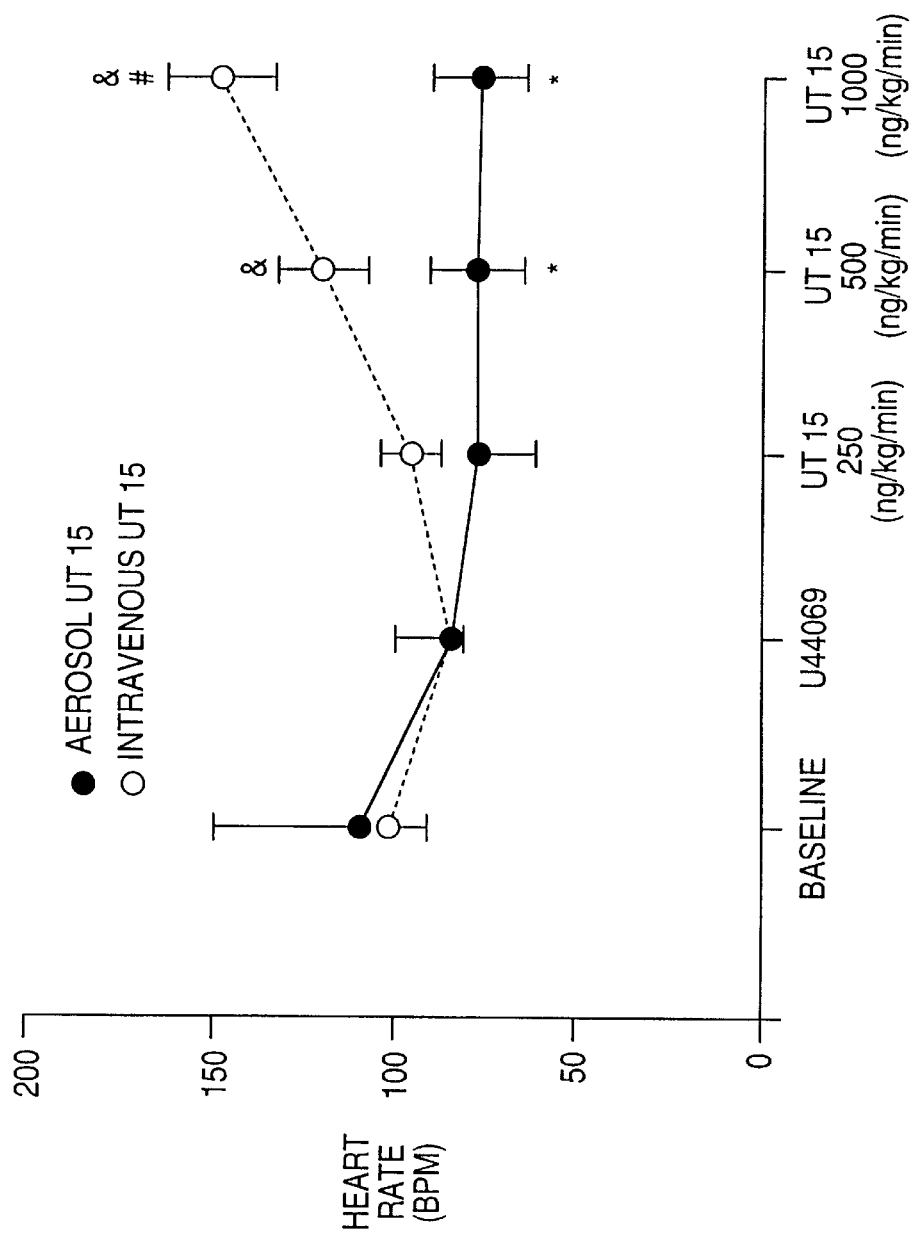
FIG. 10 is the dose-response effect on the heart rate of intravenously infused UT15 and aerosolized UT15 during intravenously infused U44069.

No differences were found between 30 minute and 60 minute UT-15 delivery at each of the three rates of administration. The effects of U44069 and the subsequent dose-response effects of UT-15 during U44069 infusion on heart rate are shown in FIG. 10. Intravenous UT-15 caused heart rate to increase above the values during U44069 conditions, whereas aerosolized UT-15 had no effect on heart rate. In particular, for intravenous UT-15, the heart rate was significantly different relative to the baseline only at a delivery rate of 1000 ng per kg per min, whereas both 500 and 1000 ng per kg per min intravenous delivery of UT-15 were statistically different from the U44069 values. Both 500 and 1000 ng per kg per min aerosol delivery rates were different from their corresponding intravenous infusion delivery rates.

Figure 11:
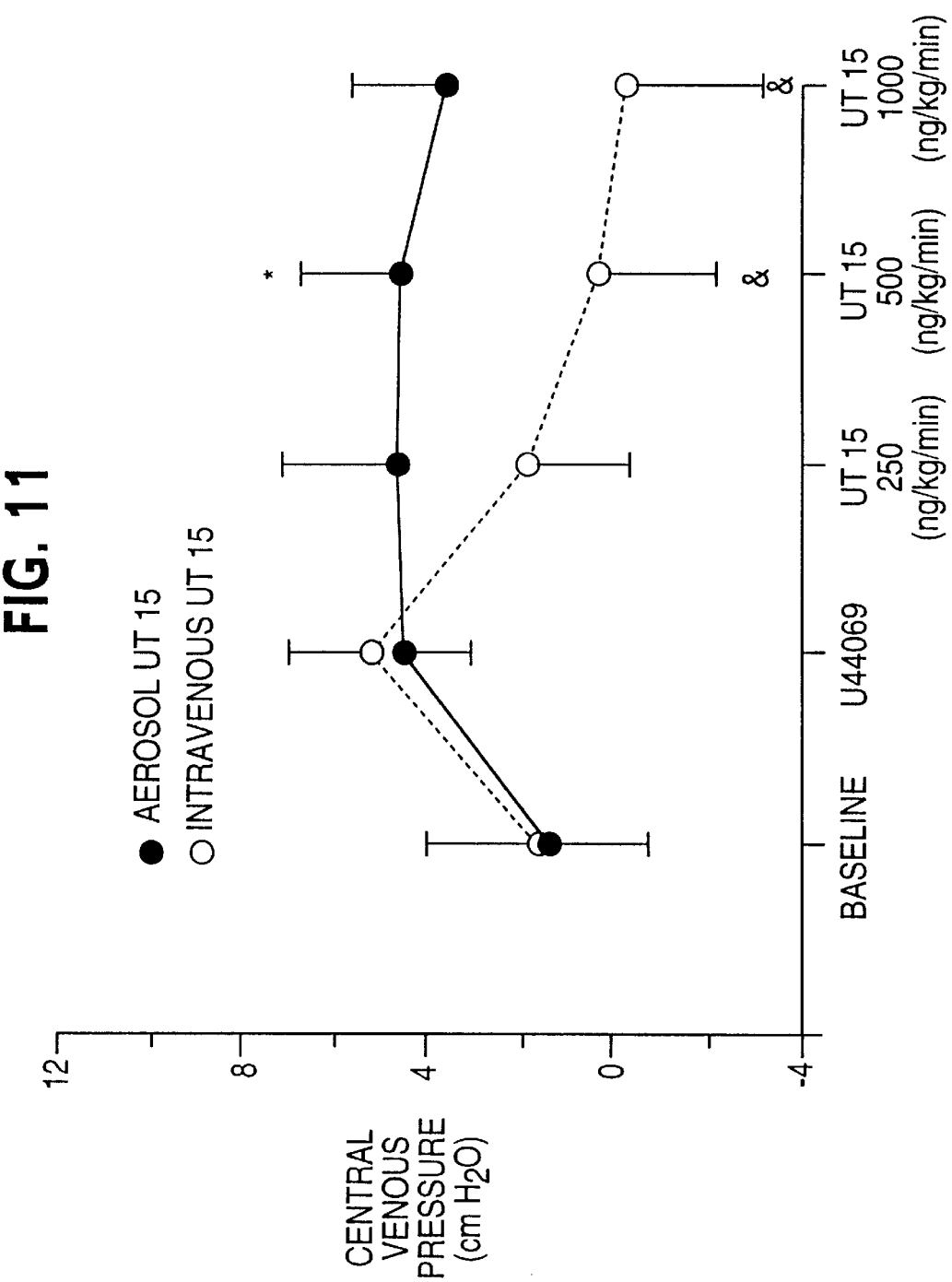
FIG. 11 is the dose-response effect of intravenously infused and aerosolized UT15 on central venous pressure during intravenously infused U44069.

Data for central venous pressure are shown by FIG. 11. Some differences were noted for central venous pressure for intravenous UT-15, in that, at 500 and 1000 ng per kg per min delivery rates the values were different from the U44069 values. Only the 500 ng per kg per min aerosol value was different from the corresponding intravenous UT-15 infusion value.

Figure 13:
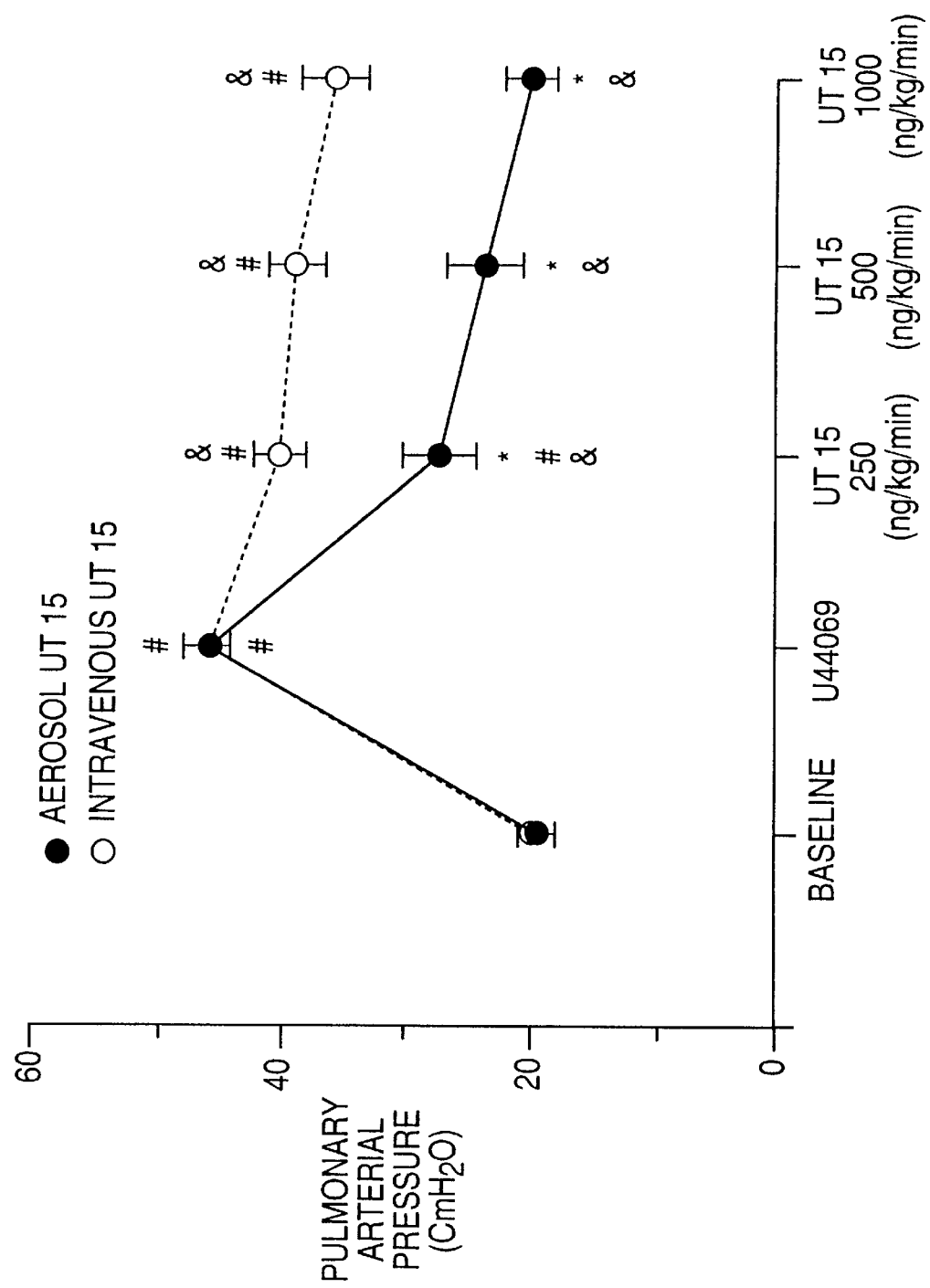
FIG. 13 is the dose-response effect of intravenously infused and aerosolized UT15 on pulmonary arterial pressure during intravenously infused U44069.

There were no statistical differences for the systemic arterial pressure for these series of experiments (FIG. 12). Pulmonary arterial pressure responses are illustrated by FIG. 13. U44069 significantly increased PPA relative baseline and all 3 delivery rates for significantly greater for aerosolized UT-15 for all 3 rates of drug delivery relative to intravenous delivery. In fact, for aerosolized UT 15 at 500 and 1000 ng per kg per min PPA was back to normal values.

Figure 14:
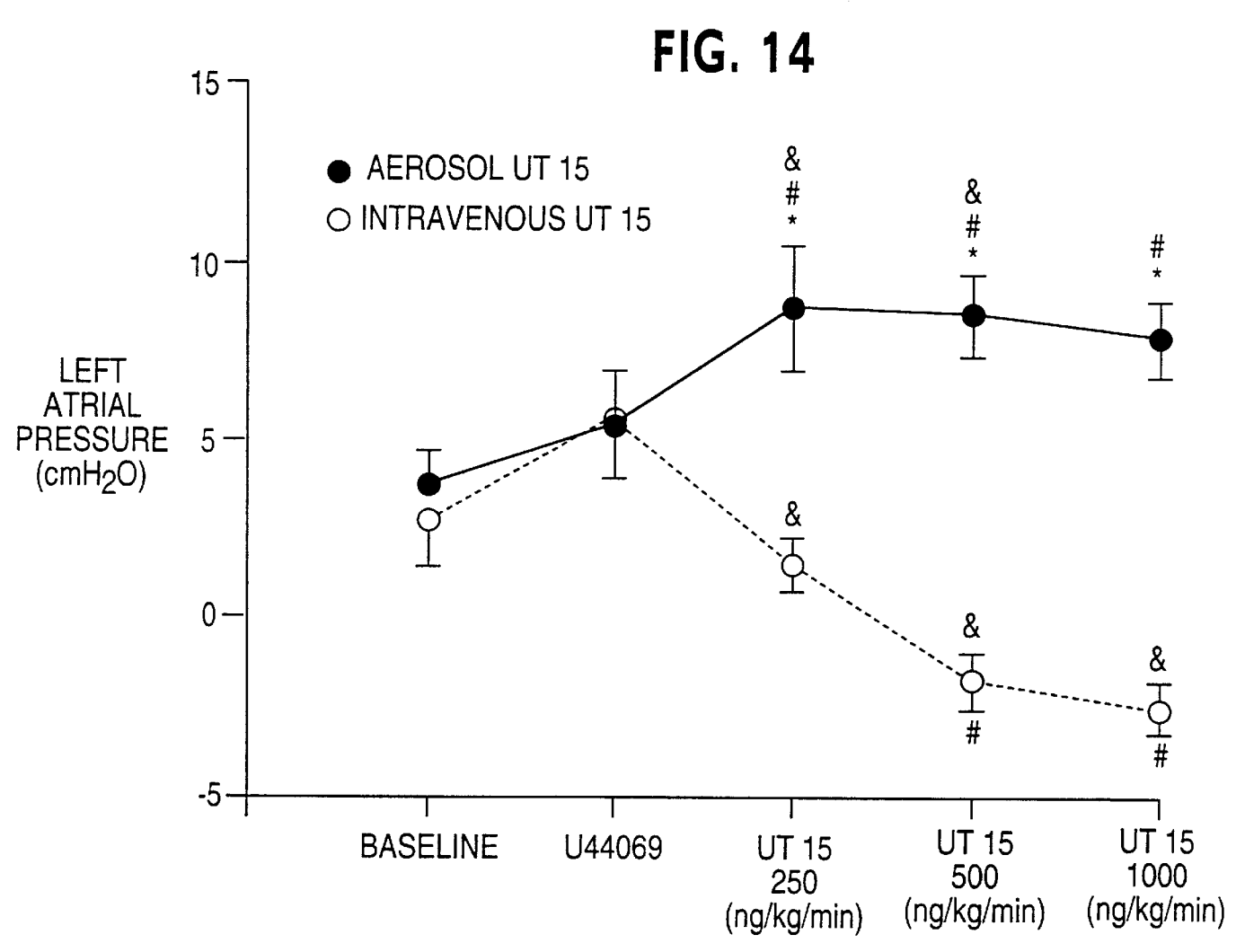

U44069 did not alter left atrial pressure significantly. However, intravenously infused UT-15 caused a significant decrease from the U44069 value at all three delivery rates and were different from the baseline values at 500 and 1000 ng per kg per min. All three aerosol delivery rates were increased above baseline, while 250 and 500 ng per kg per min were increased above the U44069 values. As can be seen from FIG. 14, all three aerosol delivery rate effects were different from the intravenously infused delivery rates.

Figure 15:
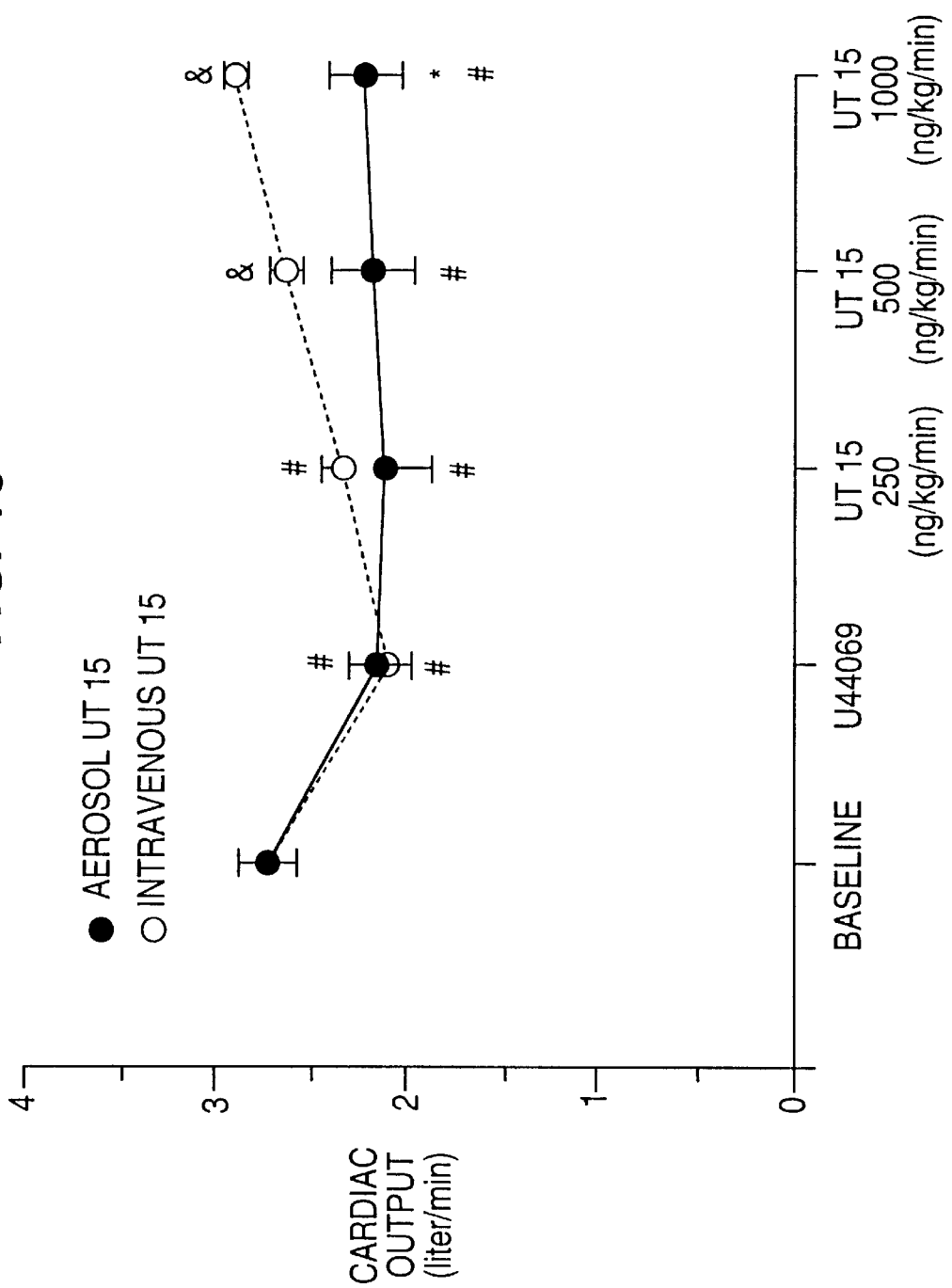
FIG. 15 is the dose-response effect of intravenously infused and aerosolized UT15 on cardiac output during intravenously infused U44069.

The most dramatic effects for UT-15 by either mode of administration were on cardiac output and the "lung variables." U44069 caused cardiac output to decrease from the baseline as depicted in FIG. 15. Aerosol UT-15 had no effect on cardiac output. Intravenous UT-15 caused a dose-response increase in cardiac output, which was significant at 500 and 100 ng per kg per min. At 1000 ng per kg per min, aerosolized UT-15 delivery was significantly different from the intravenously infused UT-15.

Figure 16:
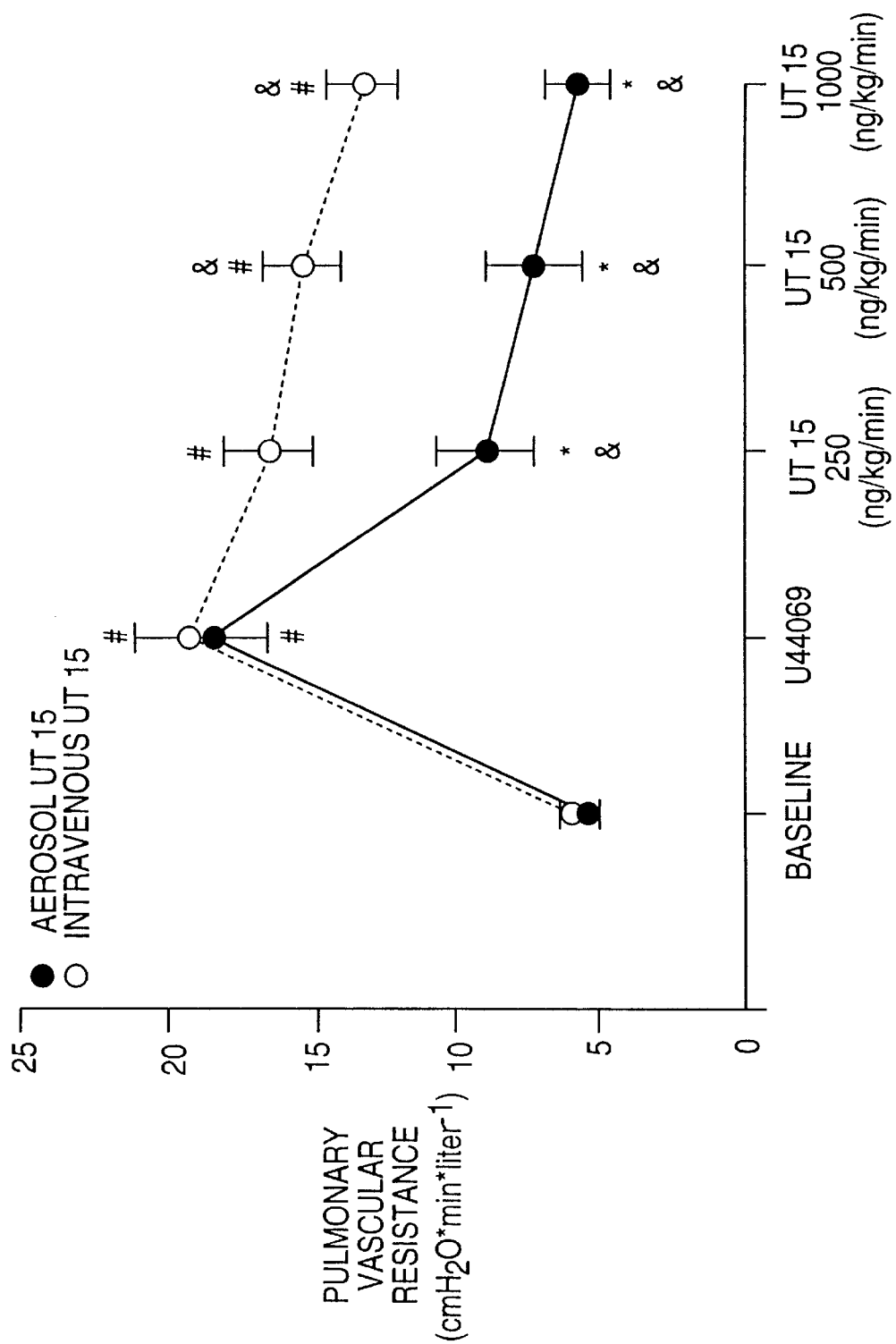
FIG. 16 is the dose-response effect of intravenously infused and aerosolized Ut15 on pulmonary vascular resistance during intravenously infused U44069.

FIG. 16 graphically demonstrates the overall effects of intravenous and aerosol delivery of UT-15 on pulmonary vascular resistance during U44069. It shows that pulmonary vascular resistance, while being significantly attenuated by both intravascularly infused and aerosolized UT-15, was more affected by aerosolized UT-15. In particular, U44069 caused a dramatic increase in PVR, which was significantly attenuated at 500 and 1000 ng per kg per min for intravenously infused UT-15. Aerosolized UT-15 caused PVR to decrease such that there was no significant difference for any of the three delivery rates relative to the baseline PVR. Interestingly, the time at which intravenous and aerosol UT-15 began to attenuate the increase in PVR were very similarly (4–5 minutes), whereas the off response for aerosolized UT-15 was much longer than intravenous UT-15 (43 vs. 12 minutes).

FIG. 18 shows that although intravascular UT-15 caused PPA to decrease significantly from the UT44069 value, this decrease matched by a decrease in PLA. Therefore, the pulmonary vascular driving pressure (PPA-PLA) was unchanged.

While the invention has been described in detail and with reference to specific embodiments thereof, it will be apparent to one skilled in the art that various changes and modifications can be made therein without departing from the spirit and scope of the invention.

All references cited herein are incorporated by reference to the same extent as if each was incorporated by reference individually.

What is claimed is:

1. A method of treating peripheral vascular disease comprising administering to a mammal in need thereof by inhalation a formulation comprising a therapeutically effective amount of a benzindene prostaglandin.

2. The method of claim 1, wherein said benzindene prostaglandin is inhaled in an aerosolized form.

3. The method of claim 2, wherein said benzindene prostaglandin is UT-15.

4. The method of claim 3, wherein said aerosolized form comprises droplets less than 10 micrometers in diameter, said droplets comprising said UT-15 in a suitable pharmacologically-acceptable liquid carrier.

5. The method of claim 1, wherein the mammal is a human.

6. A method for treating pulmonary hypertension in a mammal comprising delivering to said mammal an effective amount of UT-15 or its pharmaceutically acceptable salt or ester by inhalation.

7. The method of claim 6, wherein said UT-15 is inhaled in an aerosolized form.

8. The method of claim 7, wherein said aerosolized form comprises droplets less than 10 micrometers in diameter, said droplets comprising said compound in a suitable pharmacologically-acceptable liquid carrier.

9. The method of claim 6, wherein said UT-15 is inhaled in powder form comprising particles less than 10 micrometers in diameter.

10. The method of claim 1, wherein the formulation comprises a sustained release form of a benzindene prostalandn.

11. The method of claim 6, wherein said UT-15 is a sustained release form.

12. The method of claim 1, wherein said aerosolized administration of benzindene prostaglandin has no effect on heart rate.

* * * * *

UNITED STATES PATENT AND TRADEMARK OFFICE
CERTIFICATE OF CORRECTION

PATENT NO. : 6,521,212 B1
APPLICATION NO. : 09/525471
DATED : February 18, 2003
INVENTOR(S) : Gilles Cloutier et al.

It is certified that error appears in the above-identified patent and that said Letters Patent is hereby corrected as shown below:

Col. 14, claim 8, line 17, "said compound" should be --said UT-15--.

Signed and Sealed this

Twelfth Day of January, 2010

David J. Kappos
*Director of the United States Patent and Trademark Office*